United States Patent [19]

Plyter

[11] Patent Number: 4,924,709
[45] Date of Patent: May 15, 1990

[54] TENSION TESTING TOOL
[75] Inventor: Walter J. Plyter, Maitland, Fla.
[73] Assignee: Daniels Manufacturing Corporation, Orlando, Fla.
[21] Appl. No.: 352,292
[22] Filed: May 15, 1989
[51] Int. Cl.⁵ ............................................. G01N 3/08
[52] U.S. Cl. ...................................... 73/829; 73/830
[58] Field of Search .......................... 73/159, 826–831, 73/833, 834, 856, 858, 860, 862.62, 829, 830

[56] References Cited

U.S. PATENT DOCUMENTS

| | | | |
|---|---|---|---|
| 2,217,080 | 10/1940 | Ruch | 73/829 |
| 2,535,988 | 12/1950 | Sakirsky | 73/828 |
| 2,782,635 | 2/1957 | Knight | 73/828 |
| 3,272,002 | 9/1966 | Dickman | 73/828 |
| 3,370,458 | 2/1968 | Dillon | 73/862.62 |
| 3,678,738 | 7/1972 | Jubelt | 73/827 |
| 3,887,022 | 6/1975 | Stanev | 73/862.62 |
| 4,245,512 | 1/1981 | Saunders | 73/828 |

FOREIGN PATENT DOCUMENTS

| | | | |
|---|---|---|---|
| 501951 | 4/1920 | France | 73/826 |
| 0090267 | 7/1981 | Japan | 73/827 |
| 0058337 | 4/1984 | Japan | 73/826 |

OTHER PUBLICATIONS

The Hunter Terminal Pull Tester, Hunter Spring Company, Lansdale, Pa., Bulletin 750e, Sep. 1961.

Primary Examiner—Robert R. Raevis
Attorney, Agent, or Firm—James H. Beusse

[57] ABSTRACT

A hand tool for tension testing of flexible elongated members and connections thereto comprises a drawn cup roller clutch having a shaft and a bearing assembly. The bearing assembly and the shaft are coupled for relative concentric rotation about an axis through the shaft. First and second plier-like handles are connected for affecting unidirectional rotation of the shaft with respect to the bearing assembly and are arranged in opposed relationship whereby movement of the handles towards one another effects relative rotation of the shaft and the bearing assembly in a preselected direction. A compression gauge is attached to the outer surface of an extended portion of one of the handles disposed oppositely from the handles. The gauge includes a U-shaped compression beam and a dial indicator calibrated to read force as a function of relative displacement between opposed arms of the U-shaped beam. The hand tool further comprises an apparatus attached to one of the arms of the beam for holding an end of a member to be tested for tensile strength. Another device is attached to the shaft for holding another end of the member, and is rotatable with the shaft upon closing motion of the handles to place the member in tension. The dial indicator provides a continuous indication of tension force exerted on the member.

5 Claims, 1 Drawing Sheet

TENSION TESTING TOOL

The present invention relates to manually operated tension testing tools and, more particularly, to hand tools for pull or tension testing of terminal pins attached to electrical cables.

BACKGROUND OF THE INVENTION

Various types of tension testing tools are known in the prior art ranging from relatively elaborate permanently mounted testing devices to portable hand-held devices. One known type of portable hand-held tension testing tool for wires or cables is shown in U.S. Pat. No. 2,782,635 issued to F. J. Knight on Feb. 20, 1957. In the Knight device, there is provided a hand-held tension testing tool utilizing a plier-type arrangement with a dial gauge positioned to read the amount of compressive force exerted on the opposed handles of the device in a direct reading fashion, i.e., the dial gauge is mounted to one of the arms of the plier-type device and the plunger element of the dial gauge operates against the other of the arms. The two arms of the device extend slightly beyond a pivot point with one of the arms having apparatus for attaching one end of a cable or wire and the other has apparatus for holding a solderless or crimped terminal. As illustrated in the patent, the device can be used for tensile testing of wire or for testing of the connection between a solderless terminal and a wire, providing the solderless terminal is of the type which terminates in a screw receiving end. The Knight patent does not disclose how one could use the device for testing the connection between the cable and a solderless terminal pin. Another disadvantage of the Knight device is that the connection between the cable and the terminal pin must be pulled taught prior to actuation of the handle since there is no facility for collecting any additional cable. This also requires that the force exerted by the operator on the handles of the tool be equal to the amount of force required for the testing. For larger cables, this amount of force could be relatively large and may result in undue strain by an operator.

Another type of tension testing tool is shown in U.S. Pat. No. 3,272,002 issued to W. H. Dickman on Sept. 13, 1966. The Dickman patent shows a device which has essentially a plier-like arrangement and utilizes the same type of tension testing method as disclosed by Knight, i.e., all of the force required to affect the tensioning of the cable must be applied directly by the operator of the hand tool. In Dickman, the measuring device is a breakover device which often provides relatively inaccurate readings.

SUMMARY OF THE INVENTION

It is an object of the present invention to provide a hand tool for tensile testing of flexible elongated wires or cables or terminal connections thereto which overcomes the disadvantages of the prior art devices.

It is a more specific object of the present invention to provide a hand tool for tensile testing of connector pins to electrical cables in which the cable may be accumulated on the hand tool without being first placed in a taught position.

The above and other objects, features and advantages of the present invention are disclosed in a preferred embodiment in a tension testing tool utilizing a drawn cup roller clutch having a shaft in a housing with the housing and shaft being coupled for relative concentric rotation about an axis through the shaft. First and second plier-like handles are connected respectively to the shaft and to the housing and extend in a first direction from the housing. The handles are arranged in opposed relationship whereby movement of the handles toward one another affects relative rotation of the shaft and the housing in a preselected direction. A compression gauge is attached to an outer surface of the housing opposite from the handles. The gauge includes a U-shaped compression beam and a dial indicator calibrated to read force as a function of relative displacement between opposed arms of the U-shaped beam. Apparatus is attached to one of the arms of the beam for holding it into the member to be tested for tensile strength. This apparatus is attached so as to cause relative displacement of the arms when the member is placed in tension. Additional apparatus is attached to the shaft for holding another end of the member with the additional apparatus being rotatable with the shaft upon closing motion of the handles to place the member in tension. The dial indicator is adapted to provide a continuous indication of tension force exerted on the member. In one form, the apparatus for holding the terminal end of the cable comprises a substantially circular plate having a plurality of circumferentially spaced slots of different selected sizes for receiving different sizes of terminal pins. The plate is attached for rotation about a central axis for selectively positioning at least one of the slots in alignment with the rotatable apparatus connected to the handles. The rotatable apparatus is a generally tubular shaped member having an aperture passing through a diameter thereof for receiving and retaining an end of a wire or cable. The wire cable is collected around the tubular member as the handles are successively opened and closed. The mechanical advantage gained by the lever operated rotating shaft minimizes the force required to operate the tool.

BRIEF DESCRIPTION OF THE DRAWINGS

For a better understanding of the present invention, reference may be had to the following detailed description taken in conjunction with the accompanying drawings in which.

DETAILED DESCRIPTION

Figure 1:
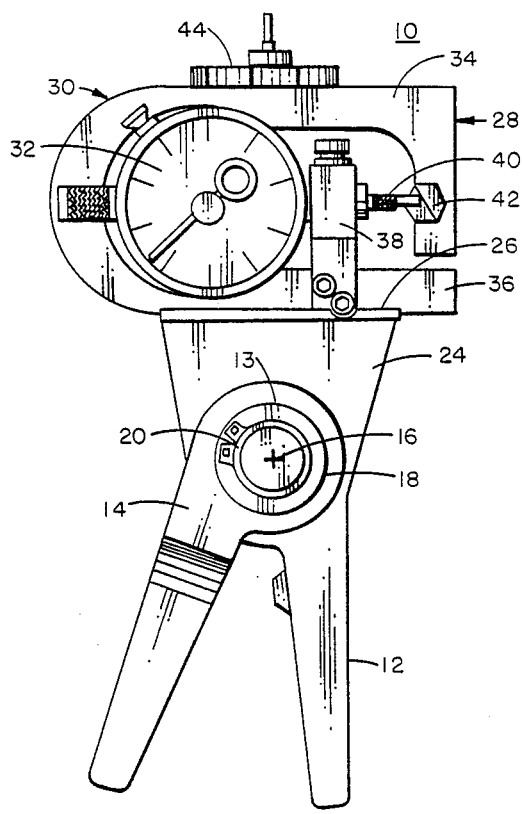
FIG. 1 is a side elevation of a tension testing tool in accordance with one form of the present invention.
Figure 2:
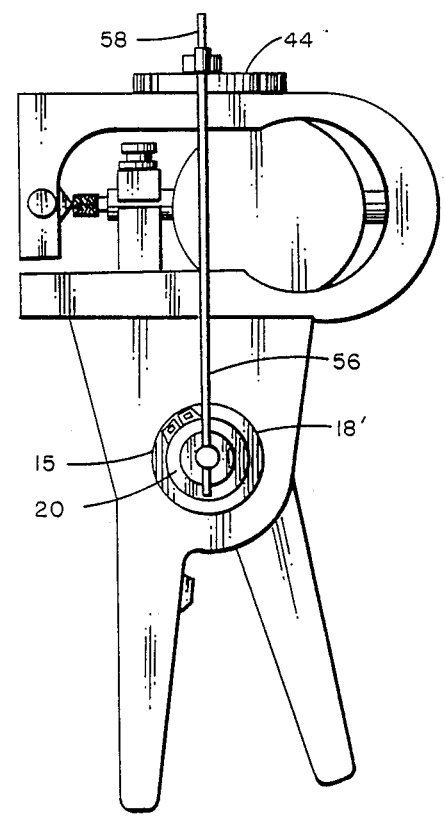
FIG. 2 is a side elevation view of the tension testing tool of FIG. 1 taken from the opposite side thereof with a wire or cable in position for tension testing.
Figure 4:
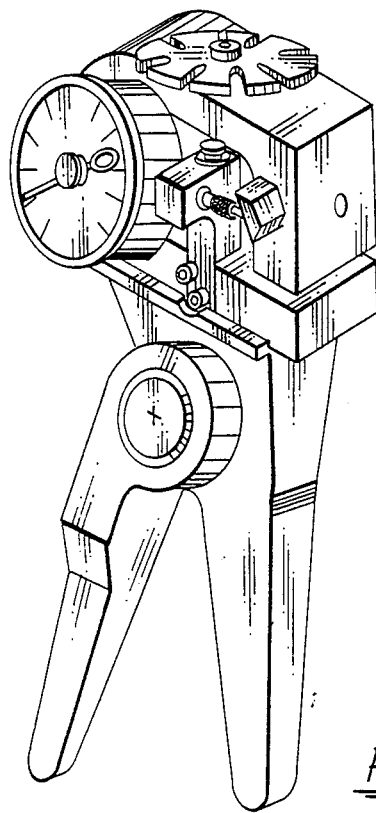
FIG. 4 is a perspective view of the tension testing tool of FIG. 1.

Referring to FIGS. 1 and 2, the tension testing tool, indicated generally at 10, comprises first and second handle members 12 and 14 joined together at a pivot point 16. The handles 12 and 14 are assembled in a plier-like arrangement utilizing a pair of unidirectionally rotatable members having a common shaft extending through corresponding apertures 13, 15 in the two handles about the axis 16. The unidirectional rotating members are indicated at 18, 18' and preferably comprises a drawn cup roller clutch and bearing assembly. Such roller clutch and bearing assembly are commercially available items which can be obtained from, for example, Torrington Manufacturing, Inc. The drawn cup roller clutch transmits torque between a shaft and housing in one direction and allows free overrun in an opposite direction. In the illustrative figures, the shaft is indicated at 20 within the bearing assemblies indicated at 18, 18'. The housing assembly for each bearing assembly comprises the adjacent portions of the corresponding one of the apertures 13, 15 in respective handles 14, 12. The bearing assemblies 18, 18' are press fit into the corresponding one of the apertures 13, 15. The clutch and bearing assemblies are arranged for reverse directions of rotation, i.e., shaft 20 rotates freely in a clockwise direction in bearing assembly 18 and in a counterclockwise direction in bearing assembly 18'. As handle 12 is moved toward handle 14, shaft 20 rotates counterclockwise. As handle 12 is released and allowed to return to the position shown in the drawings, shaft 20 is prevented from rotating clockwise by being locked by the bearing assembly in handle 14. A return spring (not shown) may be provided to return the handles 12, 14 to their spaced relations as shown in the drawings figures.

The handle 12 has an extended portion 24 which extends in an opposite direction as the remainder of the handle from the pivot point 16. The extended portion 24 terminates in a substantially flat mounting surface 26. A compression gauge 28 is attached to the flat upper surface 26 of the handle 12. The compression gauge preferably comprises a U-shaped compression member 30 and a dial gauge 32. The U-shaped member 30 includes first and second opposed arms 34 and 36. The gauge assembly is mounted such that the arm 36 lies on and parallel to the mounting surface 26. The opposite arm 34 of the U-shaped compression member also lies in a plane parallel to the surface 26. The gauge is mounted to the compression member by a support member 38 attached to the lower arm 36. The support member 38 extends upward and is adapted to be fastened to the housing of the dial gauge 32. The dial gauge 32 includes an indicator plunger 40 which rests against a slanted anvil 42 at the open end of the U-shaped compression member 28. Under compression loads, the two halves of the U-shaped member 28 tend to close causing the anvil 42 to force the plunger 40 inward towards the fixedly mounted dial gauge 32. The readings produced on the dial are in direct relation to displacement of the arms 36 and 34 of the U-shaped member and are therefore directly related to the load applied to effect the displacement. Preferably, the U-shaped compression member 28 comprises a mechanical force gauge of the type available from W. C. Dillon & Company, Inc. such as, for example, their model X-C.

Figure 3:
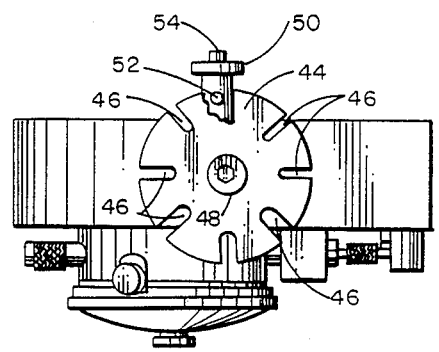
FIG. 3 is a top view of the tension testing tool of FIG. 1 showing the circular plate for receiving different sized wire or cable.

Mounted atop the arm 34 of the U-shaped compression member is a circular plate 44 having a plurality of circumferentially spaced slots 46 of various different widths. As best seen in FIG. 3, the circular plate 44 overhangs each side of the arm 34 and is mounted for rotation about a central axis 48. The plate 44 can be rotated to bring different ones of the slots into alignment with the extending element 50 which is attached to the rotatable shaft 20 of the roller clutch member 18. The member 50 includes an aperture 52 which can be seen in the view of FIG. 3 looking through the cutaway portion of the rotatable circular plate 44. A push-button 54 extending from the element 50 is spring loaded and has an aperture which mates with the aperture 52 when the push-button is depressed. When a wire or cable, such as that illustrated at 56 in FIG. 2, is inserted through the aperture, the spring loaded member moves outward to catch the wire within the aperture 52 and thereby retain it from motion.

In the use of the inventive hand-held testing tool, a wire or cable such as 56 having a crimped-type connector 58 is tested by slipping the cable into an appropriate one of the slots 46 in the plate 44. The slot is selected to be sufficiently large to accept the cable 56 but sufficiently small to prevent the terminal 58 from slipping through the slot. The opposite end of the cable 56 is then placed in the aperture 52 by depressing the button 54 so that the aperture in the member 54 aligns with the aperture 52. When the button 54 is released, the two apertures become misaligned clamping the cable into the member 50. As the handles 12 and 14 are squeezed, the shaft 20 and attached member 50 rotate accumulating the cable end about the member 50 and creating tension in the cable 56 between the plate 44 and the member 50. The tension on the member 56 causes the upper arm 34 of the compression gauge to become displaced downward with respect to the lower arm 36 so that the plunger 40 is actuated by the anvil 42. As previously mentioned, the amount of displacement between arm 34 and arm 36 is a direct measurement of the tension placed on the cable 56. When the handles 12 and 14 are released, the one-way clutch prevents the tension from being released on the cable 56 while the handles separate so that additional tension can be placed on the cable by again squeezing the handles. The handles are continuously cycled until the cable breaks or separates from the terminal or until the user elects to terminate the test and cuts the cable. The guage 32 provides the maximum tension reading and can be reset after the test in a well known manner.

While the invention has been described in what is presently considered to be a preferred embodiment, other modifications and arrangements of the invention will become apparent to those skilled in the art. Accordingly, it is intended that the invention not be limited to the specifically described embodiment, but be given an interpretation commensurate with the scope of the appended claims.

What is claimed is:

1. A hand tool for tension testing of flexible elongated members and connections thereto comprising:

a drawn cup roller clutch having a shaft and a bearing assembly, said bearing assembly and said shaft being coupled for relative concentric rotation about an axis through said shaft;

first and second plier-like handles connected for affecting unidirectional rotation of said shaft with respect to said bearing assembly, said handles being arranged in opposed relationship whereby movement of said handles towards one another effects relative rotation of said shaft and said bearing assembly in a preselected direction;

a compression gauge attached to an outer surface of an extended portion of one of said handles disposed oppositely from said handles, said gauge including a U-shaped compression beam and a dial indicator calibrated to read force as a function of relative displacement between opposed arms of said U-shaped beam;

first means attached to one of the arms of said beam for holding an end of a member to be tested for tensile strength, such first means being attached so as to cause relative displacement of said arms when the member is placed in tension; and second means attached to said shaft for holding another end of the member, said second means being rotatable with said shaft upon closing motion of said handles to place the member in tension, said dial indicator providing a continuous indication of tension force exerted on the member.

2. The hand tool as set forth in claim 1 wherein said first means comprises a substantially circular plate having a plurality of circumferentially spaced slots, the slots having selected different widths for receiving different sizes of said members and connections, said plate being attached for rotation about a central axis thereof for selectively positioning at least one of said slots in alignment with said second means.

3. The hand tool of claim 2 wherein said second means comprises a tubular shaped member having an aperture passing through a diameter thereof for receiving and retaining an end of an elongated member to be tested.

4. The hand tool of claim 3 wherein said second member includes a spring loaded push-button actuated member restrained therein and adapted to exert a retaining force against a member inserted through said aperture.

5. A hand tool for pull testing of crimp type terminal pins attached to electrical cables comprising:
    a compression gauge having a U-shaped compression member and a dial gauge coupled thereto for reading relative displacement of opposed arms of the U-shaped member when one arm is pressed toward the other of the arms, the gauge being calibrated to read displacement in terms of the applied compressive force effecting the displacement;
    a plier-like apparatus having first and second handles extending from a pivot point, said first handle having a portion extending oppositely thereof and terminating in a substantially flat mounting surface, said second handle terminating at said pivot point, said U-shaped compression member being mounted to said mounting surface with said arms being substantially parallel to said surface;
    a substantially circular plate attached to an outer surface of one of said arms of said compression member distal from said flat surface, said plate having a plurality of circumferentially spaced slots of different selected widths, said plate being attached for rotation about an axis thereof such that at least one of said slots extends outwardly of said one of said arms;
    a unidirectionally rotatable device extending through said handles along said pivot point, said rotatable device having an inner and an outer element, one of said elements being attached to said first handle and the other of said elements being attached to said second handle such that plier-like motion of said handles effects relative rotation of said elements; and
    means attached to one of said elements and rotatable therewith for holding an end of a cable whereby a cable terminal pin bond can be tested by positioning the terminal pin end of the cable into a selected one of said slots in said circular plate and another end of the cable into the rotatable means whereby actuating said handles accumulates the cable on the rotatable means and tensions the terminal pin against said plate, the compression gauge providing a reading of the tensile force on the pin.

* * * * *